(12) United States Patent
Allamon et al.

(10) Patent No.: US 6,311,775 B1
(45) Date of Patent: Nov. 6, 2001

(54) PUMPDOWN VALVE PLUG ASSEMBLY FOR LINER CEMENTING SYSTEM

(75) Inventors: Jerry P. Allamon, 34 Naples La., Montgomery, TX (US) 77356; Jack E. Miller, Houston, TX (US)

(73) Assignees: Jerry P. Allamon; Shirley C. Allamon, both of Houston, TX (US)

( * ) Notice: Subject to any disclaimer, the term of this patent is extended or adjusted under 35 U.S.C. 154(b) by 0 days.

(21) Appl. No.: 09/541,526

(22) Filed: Apr. 3, 2000

(51) Int. Cl.[7] .................................................. E21B 33/16
(52) U.S. Cl. ............................................ 166/285; 166/153
(58) Field of Search .................................. 166/70, 72, 73, 166/153, 156, 285, 289, 291

(56) References Cited

U.S. PATENT DOCUMENTS

| | | | |
|---|---|---|---|
| 4,064,937 | * 12/1977 | Barrington | 166/162 |
| 4,580,632 | * 4/1986 | Reardon | 166/250 |
| 4,934,452 | * 6/1990 | Bradley | 166/153 |
| 5,018,579 | * 5/1991 | Braddick et al. | 166/291 |
| 5,413,172 | * 5/1995 | Laurel | 166/153 |
| 5,960,881 | * 10/1999 | Allamon et al. | 166/291 |
| 6,082,451 | * 7/2000 | Giroux et al. | 166/72 |

* cited by examiner

Primary Examiner—Frank S. Tsay
(74) Attorney, Agent, or Firm—McGlinchey Stafford; Clarence Eriksen

(57) ABSTRACT

Method and apparatus are disclosed for use in cementing a tubular member which is run into a borehole using a drill string. A landing collar is attached to the tubular member near the bottom of the tubular member, and the landing collar has an opening at least five inches in diameter. A liner wiper assembly is releasably suspended from the drill string. The liner wiper assembly comprises a lower liner wiper plug comprising float valves and an upper liner wiper plug. With the method and apparatus of the present invention, plugging problems are minimized.

3 Claims, 6 Drawing Sheets

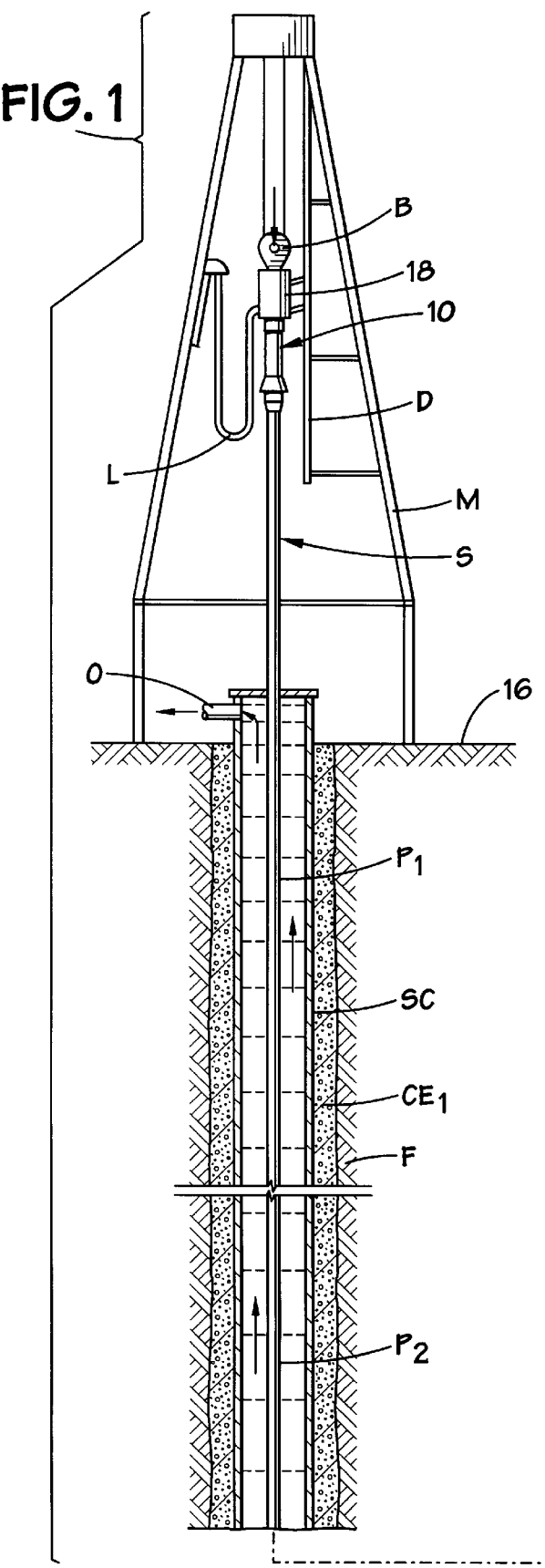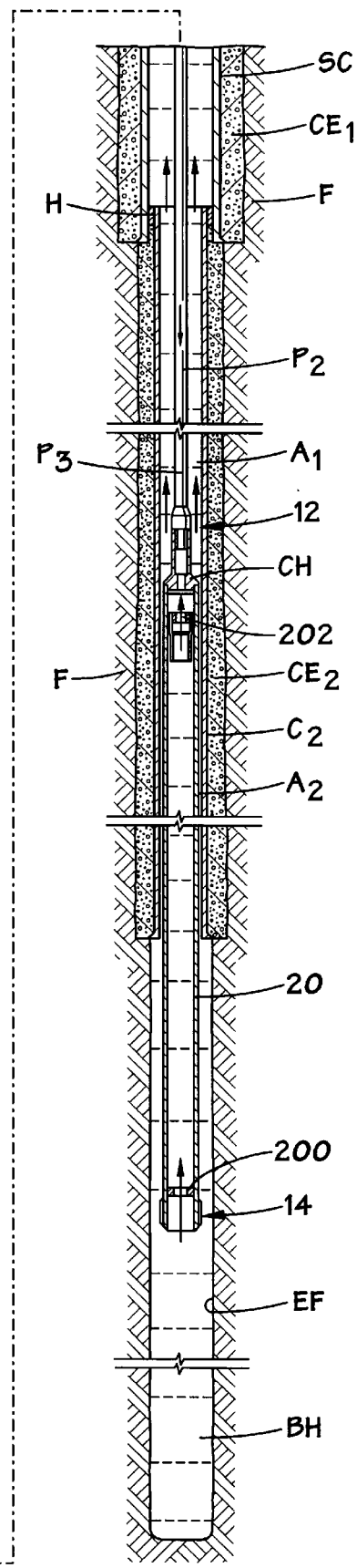
FIG. 1

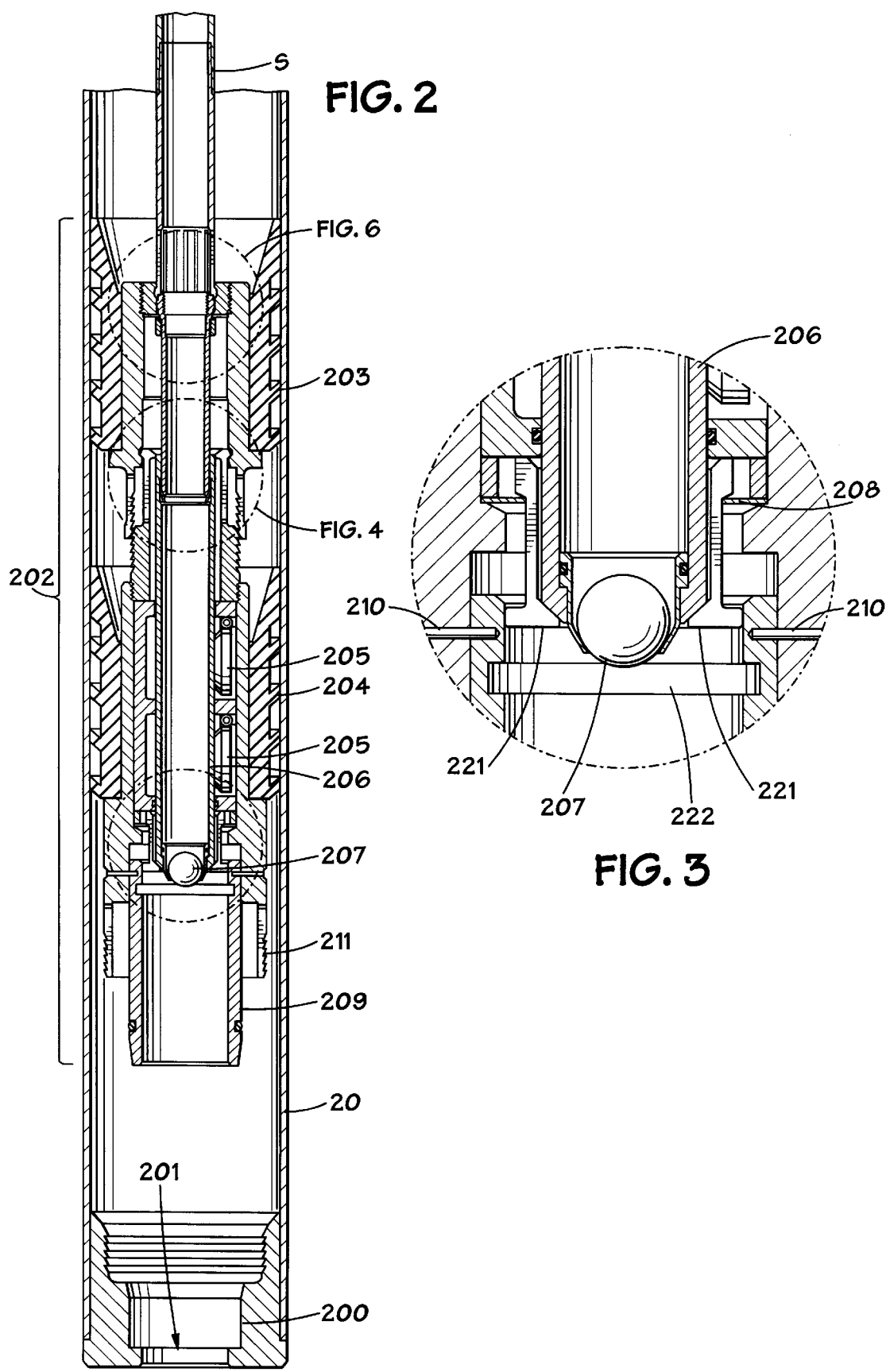

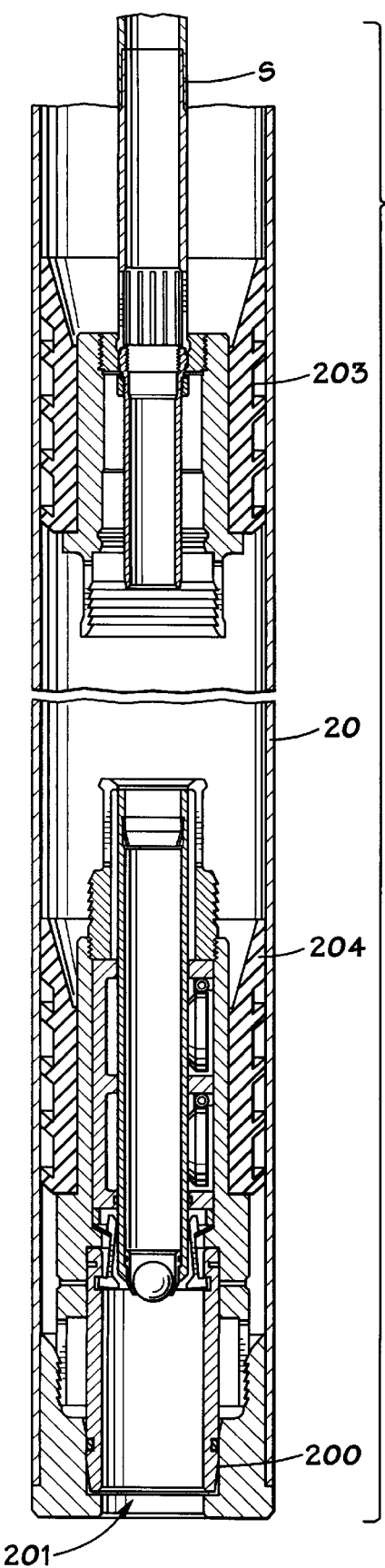
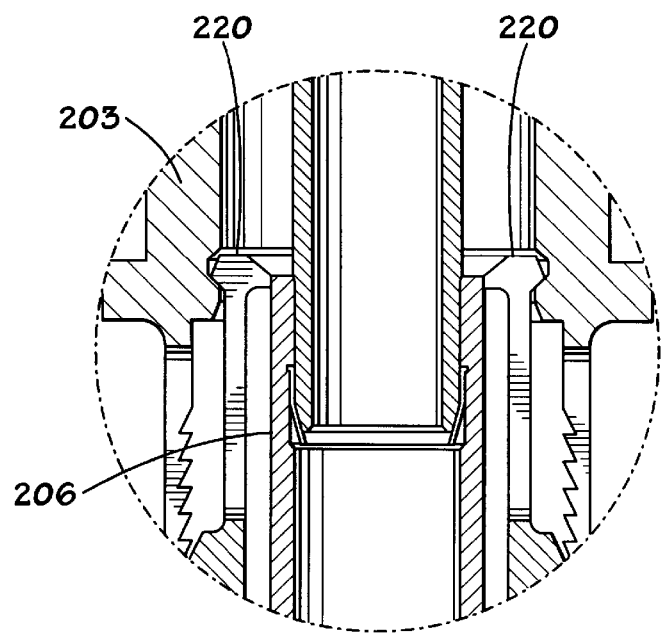
FIG. 5
FIG. 4

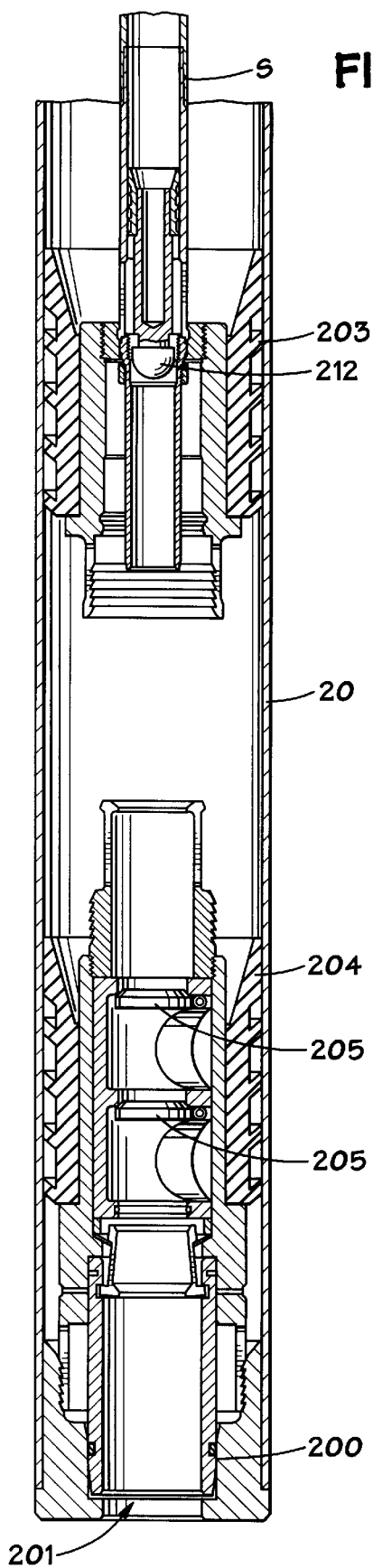
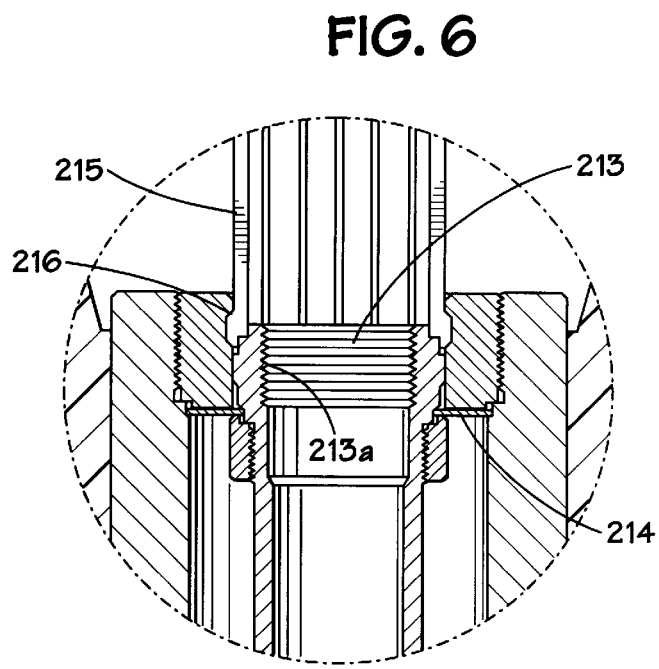
FIG. 7
FIG. 6

PUMPDOWN VALVE PLUG ASSEMBLY FOR LINER CEMENTING SYSTEM

BACKGROUND OF THE INVENTION

1. Field of the Invention

The present invention relates to apparatus for use in cementing any tubular member that is run or landed with a string of drill pipe.

2. Description of the Prior Art

Prior art liner cementing equipment includes a flapper or a float valve at the bottom of the liner. The flapper is conventionally held open by a breakable plastic tab which is actuated (i.e., broken) by a drop ball when the cementing operation is to begin. Since the drop ball which is used to activate the float valve must be small enough to pass through the drill string, the maximum float valve opening size for a 13⅜" liner may be on the order of 2 to 3" in diameter. As the liner is lowered into the well bore, the fluid in front of the liner must be displaced to flow through the bottom opening in the float valve as well as around the outside annulus defined by the well bore and the liner.

Two problems exist with respect to conventional cementing apparatus. First, the flow resistance of two above-identified flow paths may be high and thus cause a pressure buildup below the liner. This pressure buildup can: (a) cause damage to the formation; (b) result in loss of expensive drilling fluid; and (c) result in the liner sticking against the side of the borehole, which means that the liner does not go to the bottom of the hole. Second, the small opening through the float valve may, and often does, become plugged with cuttings and contaminants due to its small size and the highly contaminated environment in which it is used.

U.S. Pat. No. 5,960,881, which is incorporated herein by reference, discloses a downhole surge pressure reduction system to reduce the pressure buildup while running in liners. The system is typically located immediately above the top of the liner. Nonetheless, any plugging of the float valve at the lower end of the liner can, and very well may, render the surge pressure reduction system of the '881 patent ineffective.

The method and apparatus according to the present invention overcomes the plugging problem which has heretofore existed.

SUMMARY OF THE INVENTION

In accordance with the present invention, a tubular member is provided that includes a landing collar which is attached at the bottom of the tubular member and which has an opening therethrough. This apparatus greatly reduces the likelihood of plugging the tubular member while running in and provides for lower flow resistance of fluid entering the tubular member during lowering in the hole.

An embodiment of the present invention also includes a lower liner wiper plug and an upper liner wiper plug. The upper liner wiper plug is releasably suspended from the drill string and the lower liner wiper plug is releasably suspended from the upper liner wiper plug. The lower liner wiper plug has at least one, and preferably two float valves. Both of these wiper plugs are thus near the top of the tubular member as the tubular member is run into the borehole.

Once the tubular member has been lowered to full depth and the casing hanger has been set, the lower liner wiper plug is released from the upper liner wiper plug. Once released, the lower plug is pumped downhole by drilling fluid and thus displaces drilling mud from the bore of the tubular member through the large opening in the landing collar at the bottom of the tubular member. The lower liner wiper plug is locked into the landing collar, which results in float valves in the lower liner wiper plug being actuated. After cement has been pumped into the tubular member, the upper liner wiper plug is released from the drill string. As the upper liner wiper plug is pumped down, it forces the cement through the float valves, through the opening in the landing collar and into the annulus between the tubular member and the borehole.

BRIEF DESCRIPTION OF THE DRAWINGS

In the accompanying drawings:

FIG. 1 is an elevation view of the system of the present invention for running a casing liner into a borehole.

FIG. 2 is an elevation view in cross-section of a pump-down wiper plug assembly in accordance with the present invention.

FIG. 3 is an enlarged cross-sectional view of the apparatus within the circle of FIG. 2 designated by the numeral 3.

FIG. 4 is an enlarged cross-sectional view of the apparatus within the circle of FIG. 2 designated by the numeral 4.

FIG. 5 is an elevation view in cross-section of the apparatus of FIG. 2 after the lower liner wiper plug has been released, pumped down the casing liner, and locked into the landing collar.

FIG. 6 is an enlarged cross-sectional view of the apparatus within the circle of FIG. 2 designated by the numeral 6.

FIG. 7 is an elevation view of the apparatus of FIG. 2 which illustrates the release of the upper liner wiper plug from the drill string.

DESCRIPTION OF SPECIFIC EMBODIMENTS

Figure 8:
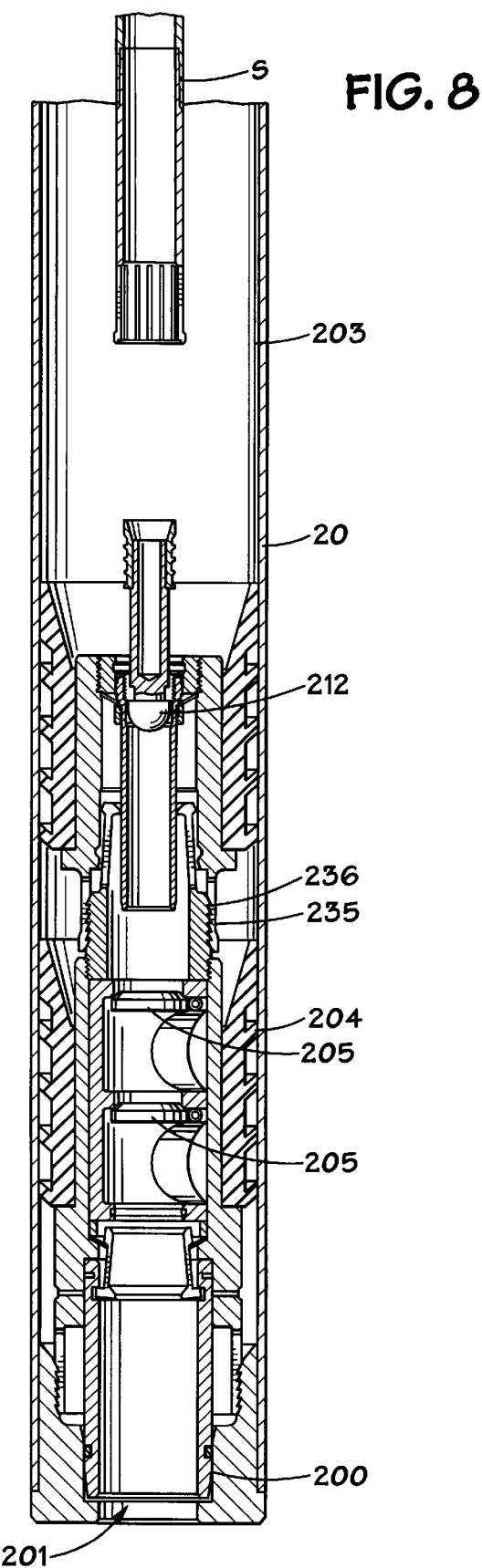
FIG. 8 is an elevation view of the apparatus of FIG. 2 after the upper liner wiper plug has been released, pumped down the casing liner and locked into the lower liner wiper plug.

In oilfield operations, a "casing liner" and a "subsea casing string" are tubular members which are run on drill pipe. The term "casing liner" is usually used with respect to drilling operations on land, while the term "subsea casing string" is used with respect to offshore drilling operations. For ease of reference in this specification, the present invention is described with respect to a "casing liner." In the appended claims, the term "tubular member" is intended to cover either a "casing liner" or a "subsea casing string."

With reference to FIG. 1, the mast M suspends a traveling block B, which supports a top drive 18, such as manufactured by Varco B.J. Drilling Systems, that moves vertically on the TDS-65 block dolly D, as is known by those skilled in the art. An influent drilling fluid line L connects the drilling fluid reservoir (not shown) to the top drive 18. Though a kelly, a kelly bushing and a rotary table are not shown, the launching manifold 10 is designed to alternatively be connected in that configuration for launching. The bottom of the manifold 10 is stabbed or threaded into a drill string, generally indicated at S, comprising a plurality of drill pipes $P_1$, $P_2$, $P_3$. The number of pipes or stands of pipes used will, of course, depend on the depth of the well.

The surface casing SC is encased by solidified cement $CE_1$, in the formation F and includes an opening O adjacent its top for controlled return of drilling fluid from up the annulus between the pipe $P_1$ and the casing SC. An intermediate casing liner C2, encased by solidified cement $CE_2$ in the formation F, is hung from the casing SC by either a mechanical or hydraulic hanger H. Casing liner 20 includes a casing liner hanger CH, and pressure is increased on casing liner 20 to actuate casing liner hanger CH to hang casing liner 20 on casing liner C2.

Referring now to FIGS. 1 and 2, in a cementing system according to the present invention, casing liner 20 includes a landing collar 200 which is attached near the bottom of casing liner 20. Landing collar 200 has an opening 201 therethrough, and the opening 201 is preferably approximately 5½" in diameter for a 13⅜" casing. Since the internal diameter of drill string S is 2" to 3", the diameter of opening 201 is approximately two times the diameter of drill string S. Landing collar 200 does not contain any float valves.

With reference still to FIG. 2, a cementing system according to the present invention includes a wiper assembly 202 which is releasably suspended to drill string S. The wiper assembly 202 comprises an upper liner wiper plug 203 which is releasably suspended from drill string S and a lower liner wiper plug 204 which is releasably suspended from upper liner wiper plug 203. Lower liner wiper plug 204 comprises at least one float valve 205 and preferably comprises a dual, redundant, set of float valves 205. During the running in process, the lower liner wiper plug 204 is suspended from an upper plug 203 near the top of the liner 20. The valves 205 are thus located near the top of the liner 20 during running in. The valves 205 are held open and protected by a tubular sleeve 206. Since the valves 205 are located near the top of the casing liner during running in, they are fairly remote from the lower, highly contaminated, area of the casing liner. The valves 205 are thus highly protected until they are actually needed.

Once the casing liner has been lowered to full depth (i.e., run in) as illustrated in FIG. 1 and the cementing process is about ready to begin, a drillable drop ball 207, which is, for example, 2¼" in diameter, is pumped downhole until it lands in a seat in the lower end of the valve opening sleeve 206, as illustrated in FIGS. 2 and 3.

Referring to FIG. 3, the landing of the ball 207 prevents flow through the valve opening sleeve 206, which allows pressure to be increased above the lower liner wiper plug 204. By increasing pressure behind the ball 207 and above the lower liner wiper plug 204, a yieldable flat washer 208 that restrains the valve opening sleeve 206 is forced to deflect and assume a "dished" shape. This relatively small deflection allows valve opening sleeve 206 to move downward. With reference to FIG. 4, the downward movement of valve opening sleeve 206 allows the plurality of fingers 220 to move inward, thereby disengaging themselves from the housing of upper liner wiper plug 203. The lower liner wiper plug 204 is thus released from its connection with the upper liner wiper plug 203.

Referring to FIGS. 2 and 5, once released from the upper liner wiper plug 203, the lower liner wiper plug 204 inclusive of float valves, may be pumped downhole by drilling fluid and thus displace the drilling mud from the bore of the casing liner 20 through the opening 201 in the landing collar 200 at the bottom of the casing liner and into the annulus 14.

Referring to FIGS. 2 and 3, the lower liner wiper plug 204 assembly is designed so that a protruding nose section 209 seals in a receiving seal bore in the landing collar 200 located at the lower end of the casing liner 20. This nose section 209 is forced upward in the lower liner wiper plug assembly to break shear pins 210. This action enables the compete release of the valve opening sleeve 206, allowing it to move further downward so that sleeve retainer fingers 221 engage annular groove 222. At this time, the float valves 205 are enabled. The shear-pinned protruding nose thus acts as an interlock to make it unlikely that the valve opening sleeve 206 will release and enable the float valves 205 prematurely due to spurious contact with debris in the liner bore. Premature float valve actuation will disrupt the cementing operation because no pressure could be built above the plug to displace it downward since the flappers would simply open.

With reference again to FIG. 2, the lower liner wiper plug 204 includes a mechanism to firmly lock it into the landing collar 200 in the form of multiple "hooked" tooth surfaces 211 that engage to resist upward motion. Resistance to upward motion is necessary since the "U-Tube" effect of the heavy cement in the annulus of the well bore against the closed flappers could impart as much as 2,500 psi differential pressure that tends to force the plug back up the casing liner 20. Once the lower liner wiper plug 204 has been pumped down and secured in connection with the landing collar 200 and the float valves 205 have been activated by pumping out the valve opening sleeve 206, the pumping of cement can be completed.

With reference to FIGS. 6 and 7, once cement pumping is complete, a drill pipe dart 212 may be inserted into the top of the drill string S and displaced downward by drilling mud so that the dart 212 acts as a barrier between drilling mud and the cement already in the drill pipe. Once the dart 212 reaches the upper liner wiper plug 203, it will land in a dart receptacle sleeve 213. The dart conventionally includes a nose section with a barbed "shark-toothed" profile "c-ring" for connection with a dart receptacle and elastomer o-ring seals. The dart receptacle sleeve 213 includes a mating tooth profile 213a for connection with the dart 212 and a seal bore for receiving the o-ring seals. In this way, the dart and the dart receptacle form a sealed mechanical connection.

A yieldable, disc-shaped, flat washer 214 supports the dart receptacle in the structure of the upper plug. The washer 214 is mounted in such a way that load imparted by the dart 212 is carried through the washer 214 and ultimately reacts in the drill string. The design allows release of the upper liner wiper plug 203 from the drill string by increasing the pressure behind the dart 212 to force the washer 214 to yield and slightly displace downward. As the washer 214 yields and displaces, it allows the dart receptacle sleeve 213 to move downward also. The dart receptacle sleeve 213 serves as the backup to steel "fingers" 215 formed onto the end of the drill string. The fingers 215 are formed such that their lower outer ends 216 include wedge surfaces, which are captured in a mating recess in the top flange portion of the upper liner wiper plug 203. As the dart receptacle displaces downward due to the force created by pressure behind the dart, the radial support for the lower finger extensions of the drill string is lost. This loss of radial support allows the wedge surfaces to force the fingers 215 inward thereby releasing the upper liner wiper plug 203 from the drill string S.

With reference to FIG. 8, once the upper liner wiper plug 203 is released from the drill string S, the upper liner wiper plug 203 with attached drill pipe dart 212 may be pumped down the casing liner thereby displacing the cement in the liner down through the dual redundant flapper valves 205 located in the lower liner wiper plug 204. The construction of the described yieldable washer release mechanism has the advantage that very little motion is needed to release the upper plug, thereby reducing the potential problem of hydraulic pressure "traps" inhibiting the disconnection process. Another advantage is that the mechanism will contain high pressure exerted below the dart since the yieldable washer 214 is completely supported against deflection upward. Still another advantage is that yielding of quite a large amount of metal is required to displace the washer the required amount to initiate the release motion, which will, provide more resistance to premature release due to rapid impact loads from dart momentum as it lands in the dart receptacle. Yet another advantage of the mechanism is that the yieldable washer, that allows the release to occur, is isolated from loads between the drill string and the plug so that plug release can only occur due to the force of the dart and not due to loadings between the plug and the drill string.

One potential problem subsequent to release of the upper liner wiper plug 203 is that the dart 213 must travel several inches downward for the dart sealing cups to clear the seal bore portion of the drill string. This travel will create an evacuated region above the plug in the annulus between the drill string and the casing liner, above the plug and below the sealed packoff between the drill string and the casing liner. Since the entire volume is full of fluid, the evacuation will cause a reduction in pressure above the plug and create a strong resistance to pumping the plug down the liner. This phenomenon is conventionally called a "hydraulic lock." In fact, the resistance caused by the hydraulic lock will be so strong as to prevent moving the dart far enough to allow fluid to fill the evacuated region. Therefore, although the plug will be mechanically disconnected from the drill string, it cannot be pumped down the liner due to being hydraulically locked.

Figure 9:
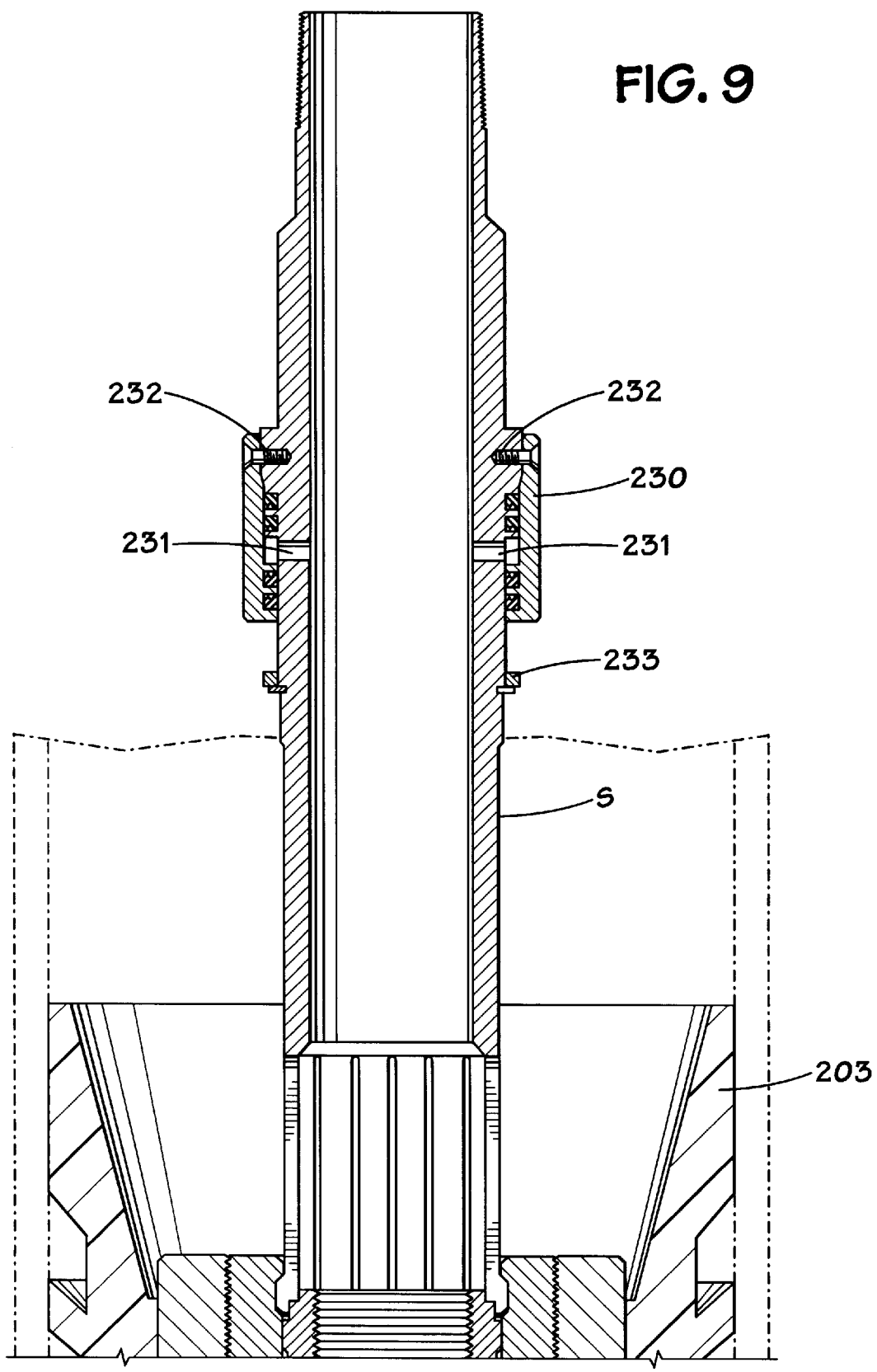
FIG. 9 is an elevation view which illustrates a mechanism to prevent hydraulic lock.

Referring to FIG. 9, a sealed sleeve 230 that defines an annular piston is provided on the outside of the drill string S. The sleeve 230 is hydraulically ported to the bore of the drill string S by a plurality of holes 231 formed in the drill string S. The sleeve 230 is held in place by shear pins 232 which may, for example, be Phillips head screws. Once differential pressure between the inside of the drill string and the evacuated annulus exceeds the predetermined allowable amount, the annular piston will create a load sufficient to shear the retaining shear pins 232, thus releasing the sleeve 230 and allowing fluid to flood into the evacuated region. The hydraulic lock will be relieved and thus the upper liner wiper plug 203 will then be free to travel downhole without resistance caused by hydraulic locking. Snap ring 233 is provided on drill string S to catch sleeve 230 once shear pins 232 have been sheared.

For the described release scenario to work properly, it is important that the plug release from the drill string before the shear pinned sleeve releases, so the design will be configured to have the plug release at an internal drill string pressure of approximately 2,500 psi and the shear pin sleeve release at approximately 3,500 psi.

Once the upper liner wiper plug 203 arrives at the bottom of the casing liner 20, it will latch onto the lower liner wiper plug 204 that was previously pumped down. The lower end of the upper liner wiper plug 203 includes fingers 235 with a "sharks-tooth" profile that latch onto a mating surface 236 on an upper mating surface of the lower liner wiper plug 204. During the liner running process when the plugs are located near the top of the liner, these mating surfaces are kept separated by the valve-opening sleeve 206. Since the valve opening sleeve 206 will have been pumped out of the lower liner wiper plug 204 earlier in the operating sequence, the teeth that connect the upper and lower plugs will be allowed to interlock thereby creating a structural connection between the two plugs.

The dual flapper valves 205 in the lower plug should prevent any "back-flow" or "u-tube" action of the cement. However, the structural connection of the upper liner wiper plug 203 to the lower liner wiper plug 204 in combination with the connection between the drill pipe dart with the upper plug provides yet another redundant barrier to "u-tubing" of the cement in the event that the flapper valves are contaminated too extensively to seal.

Once the liner wiper plugs 203 and 204 have been booth pumped to the bottom of the liner, the cement is allowed to harden, thereby completing the cementing job.

What is claimed is:

1. Apparatus for use in cementing a tubular member which is run into a borehole using a drill string, comprising:

a landing collar which does not include any float valves and which is attached to the tubular member near the bottom of the tubular member, said landing collar having an opening therethrough and said landing collar including a first locking assembly; and a liner wiper plug assembly which is releasably suspended from the drill string and which comprises an upper liner wiper plug and a lower liner wiper plug, said upper liner wiper plug being releasably suspended from the drill string and said lower liner being releasably suspended from the upper liner wiper plug, said lower liner wiper plug including (i) a second locking assembly which mates with the first locking assembly of the landing collar and (ii) at least one float valve which is actuated when the lower liner wiper plug is locked into the landing collar.

2. A method of cementing a tubular member in a borehole that is drilled in the earth for the purpose of producing hydrocarbons, comprising:

attaching a landing collar near the bottom of the tubular member, the landing collar having an opening therethrough;

suspending a releasable liner wiper plug assembly from a drill string, the liner wiper plug assembly including an upper liner wiper plug and a lower liner wiper plug, said lower liner wiper plug including at least one float valve;

running the tubular member and liner wiper plug assembly into the borehole;

releasing the lower liner wiper plug from the upper liner wiper plug;

pumping the lower liner wiper plug down the tubular member and lockingly engaging the lower liner wiper plug in the landing collar to actuate each float valve in the lower liner wiper plug;

pumping cement into the tubular member;

releasing the upper liner wiper plug from the drill string; and pumping the upper liner wiper plug down the tubular member to displace the cement into the annulus between the tubular member and the borehole.

3. Apparatus for releasing a wiper plug from a drill string, said wiper plug including a receptacle for receiving a dart, comprising:

a plurality of fingers which are formed in the end of the drill string which is lowered into a borehole, said fingers having lower outer ends that have wedge-shaped surfaces for engagement in the receptacle; and a yieldable, disc-shaped flat washer in the wiper plug which supports the receptacle and which allows the fingers to disengage from the receptacle when the dart is received and when pressure is increased behind the dart.

* * * * *